(12) United States Patent
Chen et al.

(10) Patent No.: US 7,772,445 B2
(45) Date of Patent: Aug. 10, 2010

(54) RUTHENIUM CATALYSTS FOR CATALYTIC HYDROGENATION

(75) Inventors: Xuanhua Chen, Mississauga (CA); Wenli Jia, Mississauga (CA); Kamaluddin Abdur-Rashid, Mississauga (CA); Rongwei Guo, Mississauga (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 0 days.

(21) Appl. No.: 12/168,396

(22) Filed: Jul. 7, 2008

(65) Prior Publication Data

US 2009/0023961 A1     Jan. 22, 2009

Related U.S. Application Data

(60) Provisional application No. 60/948,231, filed on Jul. 6, 2007.

(51) Int. Cl.
*C07C 29/141* (2006.01)
*C07C 29/145* (2006.01)
*C07C 35/06* (2006.01)
*C07C 35/08* (2006.01)

(52) U.S. Cl. .............. 568/814; 568/834; 568/838; 568/881; 568/883; 568/884; 568/885

(58) Field of Classification Search ............... None
See application file for complete search history.

(56) References Cited

FOREIGN PATENT DOCUMENTS

WO        WO 02/22526 A2      3/2002

OTHER PUBLICATIONS

Thoumazet et al., Organometallics (2003), 22, p. 1580-1581.*
Standfest-Hauser et al., J. Chem. Soc., Dalton Trans., (2001), p. 2989-2995.*
Database CAPLUS on STN, Acc. No. 1997:277690, Yang et al., Anales de Quimica International Edition (1997), 93(1), p. 28-38 (abstract).*
Abdur-Rashid, K.; Guo, R.; Lough, A.J.; Morris, R.H. Adv. Synth. Catal. 2005, 347, 571-579.
Abdur-Rashid, K.; Lough, A.J.; Morris, R.H. Organometallics 2001, 20, 1047-1049.
Abdur-Rashid, K.; Lough, A.J.; Morris, R.H. Organometallics 2000, 19, 2655-2657.
Doucet, H.; Ohkuma, T.; Murata, K.; Yokozawa, T.; Kozawa, M.; Katayama, E.; England, A.F.; Ikariya, T.; Noyori, R. Angew. Chem., Int. Ed. 1998, 37, 1703-1707.
Guo, R.; Lough, A.J.; Morris, A.J.; Song, D. Organometallics 2005, 24 3354-3354.
Guo, R.; Lough, A.J.; Morris, R.H.; Song, D. Organometallics 2004, 23, 5524-5529.
Liptau, P.; Carmona, D.; Oro, L.A.; Lahoz, F.J.; Kehr, G.; Erker, G. Eur. J. Inorg. Chem. 2004, 4586-4590.
Mikami, K.; Korenaga, T.; Terada, M.; Ohkuma, T.; Pham, T.; Noyori, R. Angew. Chem., Int. Ed.. 1999, 38, 495-497.
Ohkuma, T.; Ooka, H.; Ikariya, T.; Noyori, R. J. Am. Chem. Soc. 1995, 117, 10417-10418.
Ohkuma, T.; Koizumi, M.; Doucet, H.; Pham, T.; Kozawa, M.; Murata, K.; Katayama, E.; Yokozawa, T.; Ikariya, T.; Noyori, R. J. Am. Chem. Soc. 1998, 120, 13529-13530.
Ohkuma, T.; Doucet, H.; Pham, T.; Mikami, K.; Korenaga, T.; Terada, M.; Noyori, R. J. Am. Chem. Soc. 1998, 120, 1086-1087.
Ohkuma, T.; Ooka, H.; Yamakawa, M.; Ikariya, T.; Noyori, R. J. Org. Chem. 1996, 61, 4872-4873.
Standfest-Hauser, C.; Slugove, C.; Mereiter, K.; Schmid, R.; Kirchner, K.; Xiao, L.; Weissensteiner, W.J. J. Chem. Soc., Dalton Trans. 2001, 2989-2995.

* cited by examiner

*Primary Examiner*—Brian J Davis
(74) *Attorney, Agent, or Firm*—Bereskin & Parr LLP/E.N.C.R.L., s.r.l.; Michael Fenwick (57) ABSTRACT

The present disclosure relates to a process for the hydrogenation of compounds comprising one or more carbon-oxygen (C=O) double bonds, to provide the corresponding alcohol, comprising contacting the compound with hydrogen gas at and a catalyst comprising a ruthenium-aryl-aminophosphine complex.

38 Claims, 3 Drawing Sheets

RUTHENIUM CATALYSTS FOR CATALYTIC HYDROGENATION

This application claims the benefit under 35 USC §119(e) from U.S. Provisional patent application Ser. No. 60/948,231, filed Jul. 6, 2007, which is incorporated herein by reference.

FIELD OF THE DISCLOSURE

The present disclosure relates to the field of catalytic hydrogenation, in particular where a catalytic system comprising a ruthenium-aryl-aminophosphine complex and hydrogen gas is used for the reduction of compounds containing a carbon-oxygen (C=O) double bond in the presence of a base.

BACKGROUND OF THE DISCLOSURE

Catalytic hydrogenation is a fundamental reaction in chemistry, and is used in a large number of chemical processes. Catalytic hydrogenation of ketones and aldehydes are useful and indispensable processes for the synthesis of alcohols, which are valuable end products and precursor chemicals in the pharmaceutical, agrochemical, flavor, fragrance, material and fine chemical industries.[1]

To achieve a catalytic hydrogenation transformation in the reduction of ketones and aldehydes, molecular hydrogen ($H_2$) is used. However, for the hydrogenation process to proceed, a catalyst or catalytic system is needed to activate the molecular hydrogen.

Noyori and co-workers developed the versatile $RuCl_2(PR_3)_2$(diamine) and $RuCl_2$(diphosphine)(diamine) hydrogenation catalyst system that are highly effective for the hydrogenation of ketones.[2] It was subsequently discovered that the Noyori catalysts were effective for the reductive hydrogenation of imines to amines.[3] It has been reported that ruthenium aminophosphine complexes of the type $RuCl_2$(aminophosphine)$_2$ and $RuCl_2$(diphosphine)(aminophosphine) are also very effective catalysts for the hydrogenation of ketones, aldehydes and imines, including the preparation of chiral compounds.[4] Hence, these catalysts are a versatile alternative to the Noyori-type catalysts.

The complex $RuCl_2$(aminophosphine)$_2$ can be prepared using various methods. Refluxing a basic 2-propanol solution of [$RuCl_2$(cod)] with stoichiometric amounts of the aminophosphine ligand results in the crystalline product. Refluxing a mixture of $RuCl_2(dmso)_4$ with two equivalents of the aminophosphine ligand in toluene also results in the catalyst. In addition, refluxing a mixture of $RuCl_3(PPh_3)_3$ and greater than two equivalents of the aminophosphine ligand also results in an excellent yield of the bisaminophosphine product.

The synthesis of [RuCl(p-cymene)((R,Sp)-2-[1-(N,N'-dimethylamino)ethyl]-1-diphenylphosphinoferrocene)]Cl has been reported and it was found that these compounds are active for the transfer hydrogenation of ketones in basic 2-propanol solutions under refluxing conditions.[5]

SUMMARY OF THE DISCLOSURE

It has now been found that air-stable ruthenium-aryl-aminophosphine complexes and hydrogen gas are efficient for the catalytic reductive hydrogenation of compounds containing a carbon-oxygen (C=O) double bond.

Therefore, the present disclosure includes a process for the hydrogenation of compounds comprising one or more carbon-oxygen (C=O) double bonds comprising contacting the compound with hydrogen gas and a catalyst comprising a ruthenium-aryl-aminophosphine complex in the presence of a base.

In an aspect of the disclosure, the compound comprising a carbon-oxygen (C=O) is a compound of formula (I):

wherein, $R^1$ and $R^2$ each simultaneously or independently are selected from H, $C_{1-20}$alkyl, $C_{2-20}$alkenyl, $C_{2-20}$alkenyl, $C_{3-20}$cycloalkyl, $C_{3-20}$cycloalkenyl, $C_{6-14}$aryl and heteroaryl, said latter 7 groups being optionally substituted, or $R^1$ and $R^2$ are linked to form, together with the carbon atom to which they are attached, an optionally substituted monocycle or optionally substituted polycyclic ring system; one or more of the carbon atoms in the alkyl, alkenyl, alkynyl, cycloalkyl and cycloalkenyl groups is optionally replaced with a heteromoiety selected from O, S, N, $NR^c$, $PR^cSiR^c$, and $SiR^cR^d$;

the optional substituents are selected from =O, halo, $OR^c$, $NR^cR^d$ or $R^e$;

$R^c$ and $R^d$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl; and $R^e$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl.

Hydrogenation of compounds of formula I using the process of the disclosure provides the corresponding alcohols of formula (I'):

wherein $R^1$ and $R^2$ are defined as in formula (I).

In one aspect of the disclosure, the process is characterized by the use of a ruthenium-aryl-aminophosphine complex of the formula wherein X is a suitable anionic ligand and may be the same or different;

A is optionally substituted $C_{6-14}$aryl or heteroaryl;

($PNH_2$) represents an aminophosphine ligand of formula (III):

wherein $R^3$ and $R^4$ each simultaneously or independently are selected from H, $C_{1-20}$alkyl, $C_{2-20}$alkenyl, $C_{2-20}$alkynyl, $C_{3-20}$cycloalkyl, $C_{3-20}$cycloalkenyl, $C_{6-14}$aryl, heteroaryl, $OR^5$ and $NR^5R^6$, said latter 9 groups being optionally substituted, or $R^3$ and $R^4$ are linked together to form an optionally substituted monocyclic or polycyclic ring system having 4 or more atoms, including the phosphorous atom to which said groups are bonded, and in which one or more carbon atoms in said monocyclic or polycyclic ring system is optionally replaced with a heteromoiety selected from O, S, N, $NR^5$, $SiR^5$ and $SiR^5R^6$;

L is selected from $C_{1-10}$alkylene, $C_{2-10}$alkenylene, $C_{2-10}$alkynylene, $(C_{6-14}arylene)_m$, $C_{1-10}$alkylene-$C_{6-14}$arylene, $C_{6-14}$arylene-$C_{1-10}$alkylene and $C_{1-10}$alkylene-$(C_{6-14}arylene)_m$-$C_{1-10}$alkylene, said latter 7 groups being optionally substituted;

m is 1, 2 or 3;

the optional substituents are selected from one or more of halo, $OR^5$, $NR^5R^6$ and $R^7$; and $R^5$ and $R^6$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl; and $R^7$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl.

An advantage of the ruthenium-aryl-aminophosphine complex of the present disclosure is that the ruthenium complexes form air-stable salts. In addition, the catalysts of the present disclosure require only one aminophosphine ligand per ruthenium.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in greater detail with reference to the following drawings in which.

DETAILED DESCRIPTION OF THE DISCLOSURE

Definitions

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl group.

The term "$C_{2-n}$alkenyl" as used herein means straight and/or branched chain, unsaturated alkyl groups containing from two to n carbon atoms and one or more, suitably one to three, double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl group.

The term "$C_{2-n}$alkynyl" as used herein means straight and/or branched chain, unsaturated alkyl groups containing from one to n carbon atoms and one or more, suitably one to three, triple bonds, and includes (depending on the identity of n) ethynyl, 1-propynyl, 2-propynyl, 2-methylprop-1-ynyl, 1-butynyl, 2-butynyl, 3-butynyl, 1,3-butadienyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl4-methylpent-2-ynyl, 1-hexynyl and the like, where the variable n is an integer representing the largest number of carbon atoms in the alkynyl group.

The term "$C_{3-n}$cycloalkyl" as used herein means a monocyclic or polycyclic saturated carbocyclic group containing from three to n carbon atoms and includes (depending on the identity of n), cyclopropyl, cyclobutyl, cyclopentyl, cyclodecyl, bicyclo[2.2.2]octane, bicyclo[3.1.1]heptane and the like, where the variable n is an integer representing the largest number of carbon atoms in the cycloalkyl group.

The term "$C_{3-n}$cycloalkenyl" as used herein means a monocyclic or polycyclic carbocylic group containing from three to n carbon atoms and one or more, suitably one or two, double bonds and includes (depending on the identity of n), cyclopropenyl, cyclobutenyl, cyclopentenyl, cyclodecevyl, bicyclo[2.2.2]oct-2-ene, bicyclo[3.1.1]hept-2-ene and the like, where the variable n is an integer representing the largest number of carbon atoms in the cycloalkenyl group.

The term "$C_{6-n}$aryl" as used herein means a monocyclic or polycyclic carbocyclic ring system containing from 6 to n carbon atoms, at least one aromatic ring and optionally a metal and includes, depending on the identity of n, phenyl, naphthyl, anthracenyl, 1,2-dihydronaphthyl, 1,2,3,4-tetrahydronaphthyl, fluorenyl, indanyl, indenyl, ferrocenyl, and the like, where the variable n is an integer representing the largest number of carbon atoms in the aryl group.

The term "heteroaryl" as used herein means a monocyclic or polycyclic ring system containing one or two aromatic rings and from 5 to 14 atoms of which, unless otherwise specified, one, two, three, four or five are heteromoieties independently selected from N, $NR^c$, $SiR^c$, $SiR^cR^d$ and S, wherein $R^c$ and $R^d$ is as defined for the compounds of formula (I) and includes thienyl, furyl, pyrrolyl, pyrididyl, indolyl, quinolyl, isoquinolyl, tetrahydroquinolyl, benzofuryl, benzothienyl and the like.

The term "fluoro-substituted" with respect to any specified group as used herein means that the one or more, including all, of the hydrogen atoms in the group have been replaced with a fluorine, and includes trifluoromethyl, pentafluoroethyl, fluoromethyl and the like.

The suffix "ene" added on to any of the above groups means that the group is divalent, i.e. inserted between two other groups.

The term "ring system" as used herein refers to a carbon-containing ring system, that includes monocycles and polycyclic rings and metallocenes. Where specified, the carbons in the rings may be substituted or replaced with heteroatoms. Ring systems include saturated, unsaturated or aromatic rings, or mixtures thereof.

The term "polycyclic" as used herein means groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Process of the Disclosure

It has been found that ruthenium-aryl-aminophosphine complexes are particularly efficient catalysts for the reduction of C=O double bonds under catalytic hydrogenation conditions with hydrogen gas. In addition, the ruthenium complexes are air stable and use only one stoichiometric equivalent of aminophosphine ligand per ruthenium.

Accordingly, the present disclosure relates to a process for the reduction of compounds comprising one or more carbon-oxygen (C=O) double bonds comprising contacting the compound with hydrogen gas and a catalyst comprising a ruthenium-aryl-aminophosphine complex in the presence of a base.

The compound comprising a C=O, includes compounds having one or more C=O bonds.

In an embodiment of the disclosure, the compound comprising one or more carbon-oxygen (C=O) double bond is a compound of formula (I):

(I)

wherein, $R^1$ and $R^2$ each simultaneously or independently are selected from H, $C_{1-20}$alkyl, $C_{2-20}$alkenyl, $C_{2-20}$alkenyl, $C_{3-20}$cycloalkyl, $C_{3-20}$cycloalkenyl, $C_{6-14}$aryl and heteroaryl, said latter 7 groups being optionally substituted, or $R^1$ and $R^2$ are linked to form, together with the carbon atom to which they are attached, an optionally substituted monocycle or optionally substituted polycyclic ring system; one or more of the carbon atoms in the alkyl, alkenyl, alkynyl, cycloalkyl and cycloalkenyl groups is optionally replaced with a heteromoiety selected from O, S, N, $NR^c$, $PR^c$, $SiR^c$ and $SiR^cR^d$;

the optional substituents are selected from =O, halo, $OR^c$, $NR^cR^d$ or $R^e$;

$R^c$ and $R^d$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl; and $R^e$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene$C_{6-14}$aryl.

Reduction of compounds of formula I using the process of the disclosure provides the corresponding alcohols of formula (I'):

(I')

wherein $R^1$ and $R^2$ are defined as in formula (I).

Since $R^1$ and $R^2$ may be different, it is hereby understood that the final product, of formula (I'), may be chiral, thus possibly comprising of a substantially pure enantiomer or of a mixture of stereoisomers, depending on the nature of the catalyst used in the process and the structure of the compound of formula (I). By "substantially pure" it is meant that the product comprises at least 90% of one stereoisomer and less than 10% of other stereoisomers, suitably at least 95% of one stereoisomer and less than 5% of other stereoisomers, more suitably at least 98% of one stereoisomer and less than 2% of other stereoisomers.

It is an embodiment of the disclosure that, in the compounds of formula (I) and (I'), $R^1$ and $R^2$ each simultaneously or independently are selected from H, $C_{1-10}$alkyl, $C_{2-10}$alkenyl, $C_{2-10}$alkenyl, $C_{3-10}$cycloalkyl, $C_{3-10}$cycloalkenyl and $C_{6-10}$aryl, said latter 6 groups being optionally substituted, or $R^1$ and $R^2$ are linked to form, together with the carbon atom to which they are attached, an optionally substituted monocycle or optionally substituted polycyclic ring system;

the optional substituents are selected from =O, halo, $OR^c$, $NR^cR^d$ or $R^e$;

$R^c$ and $R^d$ are simultaneously or independently selected from H, fluoro-substituted-$C_{1-4}$alkyl, $C_{1-4}$alkyl, $C_{2-4}$alkenyl, $C_{2-4}$alkynyl, $C_{6-10}$aryl and $C_{1-4}$alkylene$C_{6-10}$aryl; and $R^e$ is selected from fluoro-substituted-$C_{1-4}$alkyl, $C_{1-4}$alkyl, $C_{2-4}$alkenyl, $C_{2-4}$alkynyl, $C_{6-10}$aryl and $C_{1-4}$alkylene$C_{6-10}$aryl.

It is a further embodiment of the disclosure that, in the compounds of formula (I) and (I'), $R^1$ and $R^2$ each simultaneously or independently are selected from H, $C_{1-6}$alkyl, $C_{2-6}$alkenyl, $C_{2-6}$alkenyl, $C_{3-8}$cycloalkyl, $C_{3-8}$cycloalkenyl, ferrocenyl and phenyl, said latter 7 groups being optionally substituted, or $R^1$ and $R^2$ are linked to form, together with the carbon atom to which they are attached, an optionally substituted monocycle or optionally substituted polycyclic ring system;

the optional substituents are selected from =O, halo, $OR^c$, $NR^cR^d$ or $R^e$;

$R^c$ and $R^d$ are simultaneously or independently selected from H, $CF_3$, $CH_3$, phenyl and benzyl; and $R^e$ is selected from $CF_3$, $CH_3$, phenyl and benzyl.

In an embodiment of the disclosure, the process is characterized by the use of a catalytic system comprising a ruthenium-aryl-aminophosphine complex of the formula (II):

(II)

wherein

X is a suitable anionic ligand and may be the same or different;

A is optionally substituted $C_{6-14}$aryl or heteroaryl;

(PNH$_2$) represents an aminophosphine ligand of formula (III):

wherein

R$^3$ and R$^4$ each simultaneously or independently are selected from H, C$_{1-20}$alkyl, C$_{2-20}$alkenyl, C$_{2-20}$alkynyl, C$_{3-20}$cycloalkyl, C$_{3-20}$cycloalkenyl, C$_{6-14}$aryl, heteroaryl, OR$^5$ and NR$^5$R$^6$, said latter 9 groups being optionally substituted, or R$^3$ and R$^4$ are linked together to form an optionally substituted monocyclic or polycyclic, ring system having 4 or more atoms, including the phosphorous atom to which said groups are bonded, and in which one or more carbon atoms in said monocyclic or polycyclic ring system is optionally replaced with a heteromoiety selected from O, S, N, NR$^5$ and SiR$^5$R$^6$;

L is selected from C$_{1-10}$alkylene, C$_{2-10}$alkenylene, C$_{2-10}$alkynylene, (C$_{6-14}$arylene)$_m$, C$_{1-10}$alkylene-C$_{6-14}$arylene, C$_{6-14}$arylene-C$_{1-10}$alkylene and C$_{1-10}$alkylene-(C$_{6-14}$arylene)$_m$-C$_{1-10}$alkylene, said latter 7 groups being optionally substituted;

m is 1, 2 or 3;

the optional substituents are selected from one or more of halo, OR$^5$, NR$^5$R$^6$ and R$^7$; and R$^5$ and R$^6$ are simultaneously or independently selected from H, fluoro-substituted-C$_{1-6}$alkyl, C$_{1-6}$alkyl, C$_{2-6}$alkenyl, C$_{2-6}$alkynyl, C$_{6-14}$aryl and C$_{1-6}$alkyleneC$_{6-14}$aryl; and R$^7$ is selected from fluoro-substituted-C$_{1-6}$alkyl, C$_{1-6}$alkyl, C$_{2-6}$alkenyl, C$_{2-6}$alkynyl, C$_{6-14}$aryl and C$_{1-6}$alkyleneC$_{6-14}$aryl.

In an embodiment of the present disclosure R$^3$ and R$^4$ each simultaneously or independently are each selected from H, C$_{1-10}$alkyl, C$_{2-10}$alkenyl, C$_{2-10}$alkynyl, C$_{3-10}$cycloalkyl, C$_{3-10}$cycloalkenyl, C$_{6-10}$aryl, heteroaryl, OR$^5$, NHR$^5$ and NR$^5$R$^6$, said latter 10 groups being optionally substituted, or R$^3$ and R$^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and NC$_{1-4}$alkyl. In a further embodiment, R$^3$ and R$^4$ each simultaneously or independently are selected from H, C$_{1-6}$alkyl, C$_{2-6}$alkenyl, C$_{2-6}$alkynyl, C$_{3-6}$cycloalkyl, C$_{3-6}$cycloalkenyl and C$_{6-10}$aryl said latter 6 groups being optionally substituted, or R$^3$ and R$^4$ are linked together to form an optionally substituted monocyclic or bicyclic, saturated, unsaturated and/or aromatic ring system having 4 to 10 atoms, including the phosphorous atom to which said groups are bonded. In another embodiment of the disclosure R$^3$ and R$^4$ each simultaneously or independently are selected from H, C$_{1-6}$alkyl, C$_{2-6}$alkenyl, C$_{2-6}$alkynyl, C$_{3-6}$cycloalkyl, and C$_{6-10}$aryl said latter 5 groups being optionally substituted, or R$^3$ and R$^4$ are linked together to form an optionally substituted monocyclic or bicyclic, saturated, unsaturated and/or aromatic ring system having 4 to 10 atoms, including the phosphorous atom to which said groups are bonded. In specific embodiments of the disclosure, R$^3$ and R$^4$ each simultaneously or independently are selected from phenyl, benzyl and C$_{1-6}$alkyl, suitably, phenyl, benzyl, methyl, ethyl, n-propyl, isopropyl, sec-butyl, tert-butyl and n-butyl.

In an embodiment of the disclosure, L is selected from C$_{1-6}$alkylene, C$_{2-6}$alkenylene and (C$_{6-14}$arylene)$_m$, said latter 3 groups being optionally substituted and m is 1 or 2. In a further embodiment L is C$_{1-6}$alkylene, suitably C$_{1-4}$alkylene, more suitably C$_{2-3}$alkylene, in each case being either unsubstituted or substituted with one or two halo or R$^6$, wherein R$^6$ is selected from fluoro-substituted-C$_{1-6}$alkyl, C$_{1-6}$alkyl, C$_{6-14}$aryl and C$_{1-4}$alkyleneC$_{6-14}$aryl; suitably phenyl, benzyl, methyl or CF$_3$. In another embodiment, L is unsubstituted C$_{2-3}$alkylene.

In a further embodiment, L is optionally substituted biphenylene or binaphthalene, more suitably unsubstituted biphenylene or binaphthalene. In another embodiment of the disclosure the biphenylene has a bond between the 2 and 2' positions and the binaphthalene has a bond between the 2 and 2' positions.

In another embodiment of the invention, L is optionally substituted C$_{6-14}$arylene or C$_{6-14}$arylene-C$_{1-6}$alkylene. In a further embodiment, L is optionally substituted C$_{6-10}$arylene or C$_{6-10}$arylene-C$_{1-2}$alkylene. In another embodiment the C$_{6-14}$arylene of the latter 2 groups is selected from phenylenyl, naphthylenyl and metallocenyl, in particular ferrocenyl. In yet another embodiment, L is optionally substituted phenylenyl, naphthylenyl, metallocenyl, phenylene-methylenyl, naphthylene-methylenyl or metallocene-methylenyl and these groups are bonded together and with the PR$^3$R$^4$ and NH$_2$ groups by attachments that are ortho to each other. In a further embodiment, the optional substituents are selected from C$_{1-4}$ alkyl and fluoro-substituted C$_{1-4}$ alkyl, suitably CH$_3$ or CF$_3$.

According to the disclosure, the optional substituents on the aminophosphine of formula III are selected from one or more of halo, OR$^5$, NR$^5$R$^6$ and R$^7$, in which R$^5$ and R$^6$ are simultaneously or independently selected from H, fluoro-substituted-C$_{1-6}$alkyl, C$_{1-6}$alkyl, C$_{2-6}$alkenyl, C$_{2-6}$alkynyl, C$_{6-14}$aryl and C$_{1-6}$alkyleneC$_{6-14}$aryl and R$^7$ is selected from fluoro-substituted-C$_{1-6}$alkyl, C$_{1-6}$alkyl, C$_{2-6}$alkenyl, C$_{2-6}$alkynyl, C$_{6-14}$aryl and C$_{1-6}$alkyleneC$_{6-14}$aryl. In embodiments of the disclosure, the optional substituents are selected from one or more of halo, OH, NH$_2$, NHR$^5$, OR$^5$, NR$^5$R$^6$ and R$^7$, in which in which R$^5$, R$^6$ and R$^7$ are simultaneously or independently selected from fluoro-substituted-C$_{1-4}$alkyl, C$_{1-4}$alkyl, C$_{2-4}$alkenyl, phenyl and C$_{1-4}$alkylenephenyl, specifically methyl, benzyl and phenyl.

In an embodiment of the disclosure, A is C$_{6-14}$aryl or heteroaryl, and is optionally substituted with 1 to 3 substituents independently selected from fluoro-substituted-C$_{1-6}$alkyl, C$_{1-6}$alkyl, C$_{2-6}$alkenyl and C$_{6-10}$aryl. In embodiments of the disclosure, A is a monocyclic or bicyclic aromatic group having between 6-10 carbon atoms and is optionally substituted with 1 to 3 substituents independently selected from fluoro-substituted-C$_{1-6}$alkyl, C$_{1-6}$alkyl, C$_{2-6}$alkenyl and C$_{6-10}$aryl. In another embodiment, A is a phenyl group optionally substituted with 1 to 3 substituents independently selected from fluoro-substituted-C$_{1-6}$alkyl, C$_{1-6}$alkyl, C$_{2-6}$alkenyl and C$_{6-10}$aryl. In embodiments of the disclosure, A is a phenyl group optionally substituted with 1 to 3 substituents independently selected from fluoro-substituted-C$_{1-4}$alkyl, C$_{1-4}$alkyl and C$_{2-6}$alkenyl. In another embodiment, A is p-cymene.

The ligands X may be the same or different and are selected from any anionic ligand, suitably halo (for example, fluoro, chloro, bromo or iodo, specifically chloro), HO$^-$, R$^8$O$^-$ and R$^8$C(O)O$^-$, wherein R$^8$ is H or C$_{1-6}$alkyl. In an embodiment of the disclosure, X is chloro.

Figure 1:
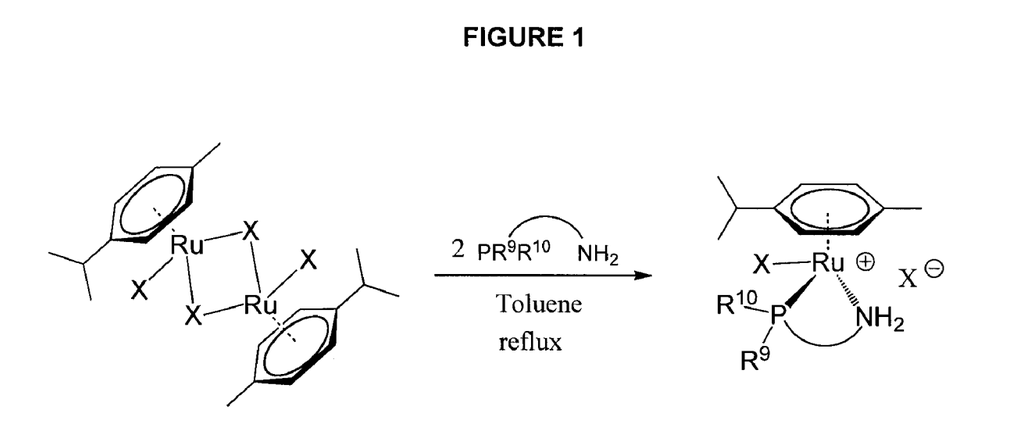
FIG. 1 is shows the preparation of a ruthenium-aryl-aminophosphine complex in an embodiment of the present disclosure.
Figure 2:
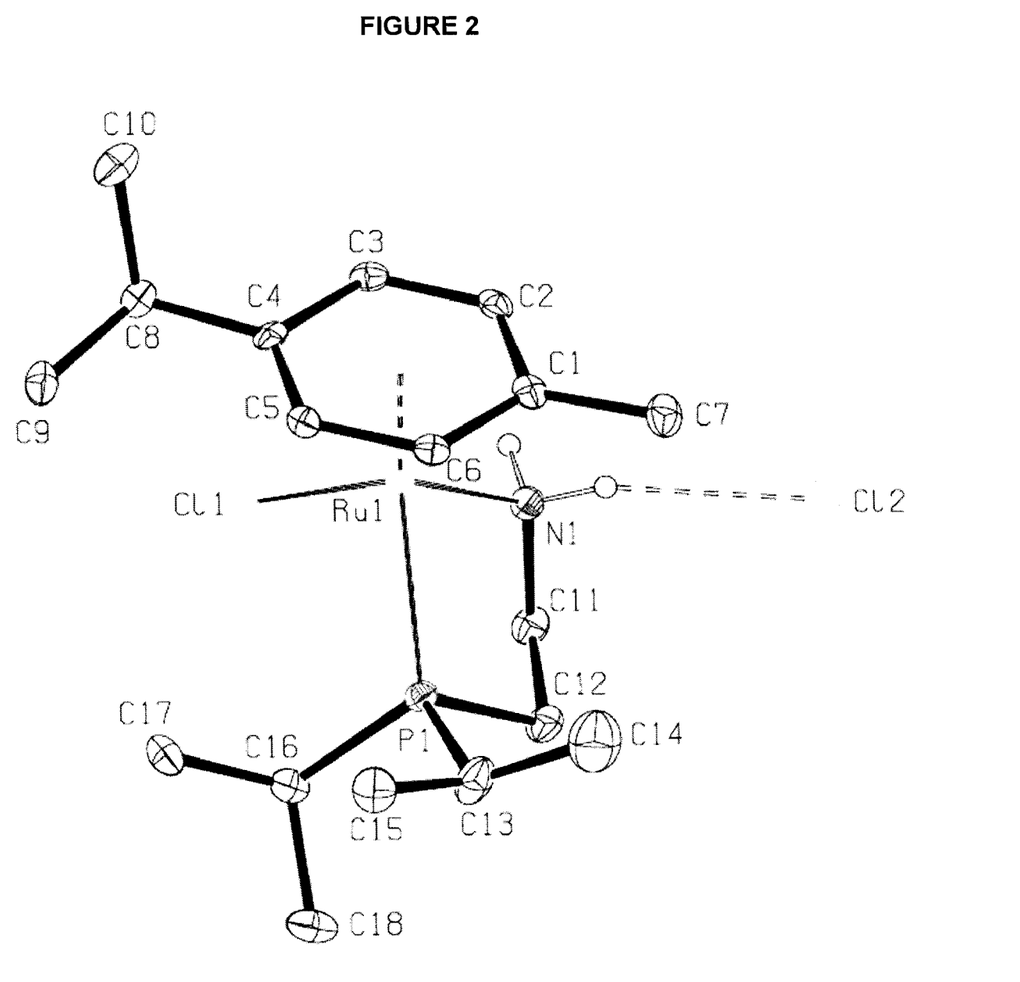
FIG. 2 shows an x-ray crystallographic structure of a ruthenium-aryl-aminophosphine complex in an embodiment of the present disclosure.
Figure 3:
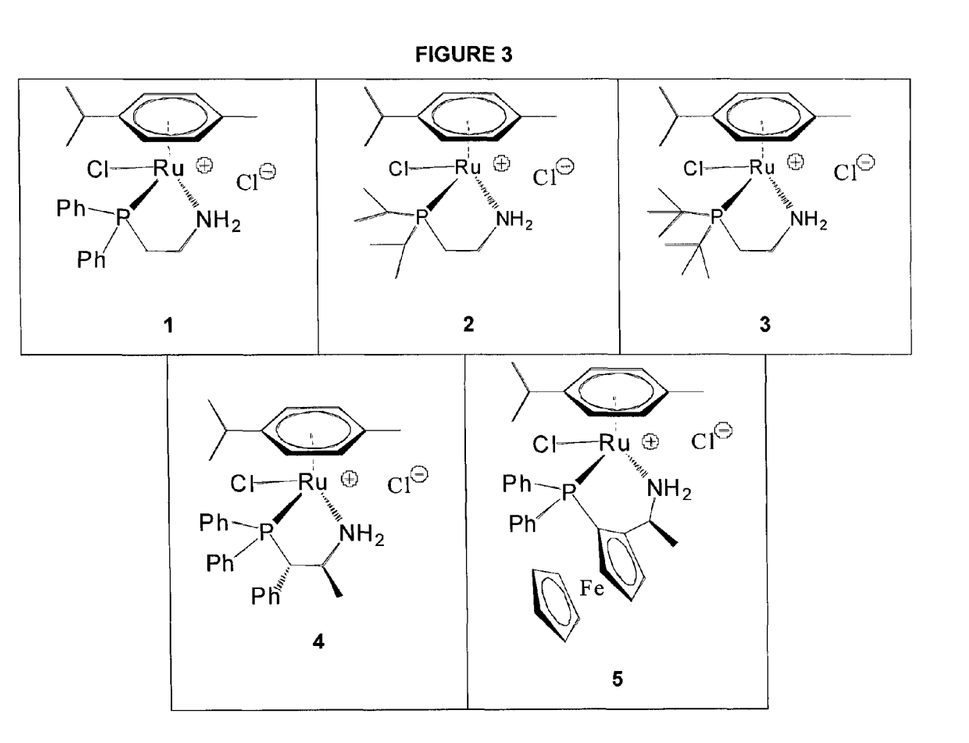
FIG. 3 shows the structure of ruthenium complexes in embodiments of the disclosure.

In a specific embodiment of the disclosure, the ruthenium aryl-aminophosphine complex of formula II is selected from compound 1, 2, 3, 4, and 5 as shown in FIG. 3.

In a general way, the complexes of formula (II) can be prepared and isolated prior to their use in the process according to the general methods described in the literature (see for example, Clarke, Z. E. et al. *Organometallics,* 2006, 25:4113-4117) or using the methods described herein.

The ruthenium complexes of formula (II) can catalytically hydrogenate compounds containing a carbon-oxygen (C=O) double bond in the presence of a base. The base can be any conventional base and one can cite, as non-limiting examples, organic non-coordinating bases such as DBU, an alkaline or alkaline-earth metal carbonate, a carboxylate salt such as sodium or potassium acetate, or an alcoholate or hydroxide salt. In an embodiment of the disclosure, the bases are the alcoholate or hydroxide salts selected from the compounds of formula $(R^{9O})_2M'$ and $R^9OM'$, wherein M' is an alkaline or alkaline-earth metal, and $R^9$ stands for hydrogen or a linear or branched alkyl group. In a further embodiment of the disclosure, $R^9$ is t-butyl and M' is potassium.

Standard catalytic hydrogenation conditions, as used herein, typically implies the mixture of the substrate with a ruthenium-aryl-aminophosphine compound of formula (II) in the presence of a base, with a solvent, and then treating such a mixture with hydrogen gas at a chosen pressure and temperature.

In an embodiment of the disclosure the hydrogen gas is used at a pressure of about 1 atm to about 100 atm, suitably about 7 atm to about 13 atm, more suitably about 10 atm.

The complexes of formula (II) can be added to the reaction medium in a large range of concentrations. As non-limiting examples, one can cite as complex concentration values those ranging from 0.1 ppm to 50,000 ppm, relative to the amount of substrate, thus representing respectively a substrate/complex (S/com or S/C) ratio of $10^7$ to 20. In an embodiment of the disclosure, the complex concentration will be comprised between 0.1 and 1000 ppm, i.e. a S/com ratio of $10^7$ to 1000 respectively. In a further embodiment of the disclosure, there will be used concentrations in the range of 0.5 to 100 ppm, corresponding to a S/com ratio of 10,000 to $2\times10^6$ respectively.

In an embodiment of the disclosure, the base may be included in a relatively large range. One can cite, as non-limiting examples, ranges between 1 to 50,000 molar equivalents relative to the complex (e.g. base/com=0.5 to 50,000), or 100 to 20,000, or even between 400 and 10,000 molar equivalents. However, it should be noted that it is also possible to add a small amount of base (e.g. base/com=1 to 3) to achieve high yields.

In the processes of this disclosure it is an embodiment that the catalytic hydrogenation reaction is carried out in the presence of a polar solvent. A wide variety of polar solvents can be used for the catalytic hydrogenation. Non-limiting examples include ethers and ester such as tetrahydrofuran, diethyl ether and ethyl acetate, primary or secondary alcohols such as methanol, ethanol and isopropanol, chlorinated solvents such as dichloromethane and chloroform, or mixtures thereof.

The temperature at which the catalytic hydrogenation can be carried out is comprised between about 0° C. and about 100° C., more specifically in the range of between about 20° C. and about 80° C. In an embodiment of the disclosure, the catalytic hydrogenation is carried out at about room temperature. Of course, a person skilled in the art is also able to select the temperature as a function of the melting and boiling point of the starting and final products.

The effectiveness of ruthenium-aryl-aminophosphine catalysts for the hydrogenation of ketones and aldehydes was investigated. The results are summarized in Tables 1-3. Table 1 shows the hydrogenation of a variety of ketones using complex 1 (FIG. 3) and KO$^t$Bu as the catalyst at room temperature. Acetophenone and benzophenone were readily converted to phenylethanol and benzhydrol, respectively. The hydrogenation of 4-tert-butylcyclohexanone was completed at room temperature and resulted in predominantly cis-4-tert-butylcyclohexanol (80%). Cis-4-tert-butylcyclohexanol is very valuable in the fragrance industry since it is used to prepare cis-4-tert-butylcyclohexyl acetate (woody acetate). The hydrogenation of the conjugated ketone benzalacetone resulted in the allyl alcohol as the only detectable product. Likewise, only the carbonyl group of 5-hexen-2-one was reduced to give the unsaturated alcohol. A 95% conversion of the ketone to the alcohol was observed in the reduction of norcamphor resulting in 75% endo-norborneol and 25% exo-norborneol. Benzaldehyde and acetyl ferrocene were converted to the respective alcohols.

Table 2 summarizes ketone hydrogenations using complex 2 (FIG. 3) as the catalyst in the presence of KO$^t$Bu. Acetophenone and 5-hexen-2-one were readily converted to phenylethanol and 5-hexen-2-ol, respectively. The hydrogenation of 4-tert-butylcyclohexanone was completed in 5 hours, resulting in 70% cis-4-tert-butylcyclohexanol, while the hydrogenation of norcamphor was 60% completed in 17 hours, resulting in 70% and 30% of the endo and exo isomers of norborneol, respectively. Benzaldehyde was converted to benzyl alcohol.

Table 3 summarizes the hydrogenation of acetophenone using complexes 3, 4 and 5 (FIG. 3) as catalysts.

While not wishing to be limited by theory, the mild reaction conditions required during the hydrogenation process using these new catalysts for the reduction of carbonyl compounds implicate the involvement of an ionic heterolytic bifunctional hydrogenation mechanism involving Ru—H and N—H moieties.

The following non-limiting examples are illustrative of the present disclosure:

EXAMPLES

All preparations and manipulations were carried out under hydrogen or argon atmospheres with the use of standard Schlenk, vacuum line and glove box techniques in dry, oxygen-free solvents. Tetrahydrofuran (THF), diethyl ether (Et$_2$O) and hexanes were purified and dried using an Innovative Technologies solvent purification system. Deuterated solvents were degassed and dried before use. Potassium tert-butoxide, aldehydes and ketones were supplied by Aldrich Chemical Company. NMR spectra were recorded on either a Varian Unity Inova 300 MHz spectrometer (300 MHz for $^1$H, 75 MHz for $^{13}$C and 121.5 for $^{31}$P) or a Bruker Avance 500 MHz DRX spectrometer. All $^{31}$P chemical shifts were measured relative to 85% H$_3$PO$_4$ as an external reference. The $^1$H and $^{13}$C chemical shifts were measured relative to partially deuterated solvent peaks but are reported relative to tetramethylsilane. The alcohol products obtained from the catalytic hydrogenation of ketones were characterized by their $^1$H and $^{13}$C NMR spectra. The aminophosphine ligands $^i$Pr$_2$PCH$_2$CH$_2$NH$_2$, $^t$Bu$_2$PCH$_2$CH$_2$NH$_2$, Ph$_2$PCH$_2$CH$_2$NH$_2$, (1R,2R)-2-amino-1-phenylpropyldiphenylphosphine and (S)-1-((R)-2-diphenylphosphino)ferrocenylethylamine) and the ruthenium salts [RuCl(p-cymene)($^i$Pr$_2$PCH$_2$CH$_2$NH$_2$)]Cl, [RuCl(p-cymene)($^t$Bu$_2$PCH$_2$CH$_2$NH$_2$)]Cl and [RuCl(p- cymene)(Ph$_2$PCH$_2$CH$_2$NH$_2$)]Cl are commercially available from Kanata Chemical Technologies Inc.

Example 1

General Procedure for Preparation of Ruthenium Complexes

A mixture of [RuCl$_2$ (p-cymene)]$_2$ (250 mg, 0.40 mmol) and the aminophosphine ligand (0.40 mmol) was refluxed in toluene (40 ml) under argon for 6 hours. The solvent was removed and ether (20 ml) was added, and the mixture stirred for 2 hours. The yellow solid was filtered, washed with ether (3×5 ml), and dried under vacuum.

Example 1.1

[RuCl(p-cymene)(Ph$_2$PCH$_2$CH$_2$NH$_2$)]Cl (1)

Yield=80%. $^1$H NMR (CD$_2$Cl$_2$), d: 1.44 (m, 1H, CH); 1.34 (d, J$_{HH}$=6.5 Hz, 3H, CH$_3$); 1.36 (d, J$_{HH}$=6.5 Hz, 3H, CH$_3$); 1.99 (s, 3H, CH$_3$); 2.32-3.21 (m, 4H); 3.34 (br, 1H, NH); 5.56 (d, J$_{HP}$=5.6 Hz, 1H, CH); 5.68 (d, J$_{HP}$=5.6 Hz, 1H, CH); 5.78 (d, J$_{HP}$=5.6 Hz, 1H, CH); 6.28 (d, J$_{HP}$=5.6 Hz, 1H, CH); 7.30-7.95 (m, 10H); 8.86 (br, 1H, NH). $^{31}$P{$^1$H} NMR (CD$_2$Cl$_2$), d: 62.5 (s).

Example 1.2

[RuCl(p-cymene)($^i$Pr$_2$PCH$_2$CH$_2$NH$_2$)]Cl (2)

Yield=86%. $^1$H NMR (CD$_2$Cl$_2$), d: 1.22 (d, J$_{HH}$=7.0 Hz, 3H, CH$_3$); 1.26 (d, J$_{HH}$=6.5 Hz, 3H, CH$_3$); 1.31 (dd, J$_{HP}$=14.1 Hz, J$_{HH}$=7.5 Hz, 3H, CH$_3$); 1.34 (dd, J$_{HP}$=10.2 Hz, J$_{HH}$=7.0 Hz, 3H, CH$_3$); 1.38 (dd, J$_{HP}$=7.1 Hz, J$_{HH}$=7.0 Hz, 3H, CH$_3$); 1.42 (dd, J$_{HP}$=14.5 Hz, J$_{HH}$=7.0 Hz, 3H, CH$_3$); 1.48 (m, 1H, CH); 1.90 (m, 1H, CH); 2.32 (s, 3H, CH$_3$); 2.36 (m, 1H, CH); 2.51 (m, 1H, CH); 2.63 (m, 1H, CH); 3.01 (m, 1H, CH); 3.00 (sept, J$_{HH}$=5.5 Hz, 1H, CH); 3.09 (br, 1H, NH); 5.49 (d, J$_{HP}$=6.0 Hz, 1H, CH); 5.75 (d, J$_{HP}$=6.0 Hz, 1H, CH); 5.80 (d, J$_{HP}$=6.0 Hz, 1H, CH); 6.61 (d, J$_{HP}$=6.0 Hz, 1H, CH); 8.43 (br, 1H, NH). $^{31}$P{$^1$H} NMR (CD$_2$Cl$_2$), d: 75.2 (s).

Example 1.3

[RuCl(p-cymene) ($^t$Bu$_2$PCH$_2$CH$_2$NH$_2$)]Cl (3)

Yield=88%. $^1$H NMR (CD$_2$Cl$_2$), d: 1.27 (d, J$_{HH}$=6.5 Hz, 3H, CH$_3$); 1.29 (d, J$_{HH}$=8.3 Hz, 3H, CH$_3$); 1.40 (d, J$_{HP}$=14.1 Hz, 9H, CH$_3$); 1.45 (d, J$_{HP}$=13.0 Hz, 9H, CH$_3$); 1.74 (m, 2H, CH); 2.45 (s, 3H, CH$_3$); 2.58 (m, 1H, CH); 3.00 (m, 1H, CH); 3.27 (sept, J$_{HH}$=6.8 Hz, 1H, CH); 3.93 (br, 1H, NH); 5.40 (d, J$_{HP}$=5.5 Hz, 1H, CH); 5.71 (d, J$_{HP}$=5.5 Hz, 1H, CH); 5.77 (d, J$_{HP}$=5.5 Hz, 1H, CH); 5.92 (d, J$_{HP}$=5.5 Hz, 1H, CH); 7.75 (br, 1H, NH). $^{31}$P{$^1$H} NMR (CD$_2$Cl$_2$), d: 87.0 (s).

Example 1.4

[RuCl(p-cymene){(R,R)(2-(diphenylphosphino)-1-phenylpropan-2-amine}]Cl (4)

Yield=82%. $^1$H NMR (CD$_2$Cl$_2$), d: 1.12-1.26 (m, 9H, CH$_3$); 1.98 (s, 3H, CH$_3$); 2.97 (m, 1H, CH); 3.24 (sept, J$_{HH}$=6.2 Hz, 1H, CH); 3.52 (m, 1H, CH); 3.71 (m, 1H, CH); 5.18 (J$_{HP}$=6.6 Hz, 1H, CH); 5.49 (d, J$_{HP}$=6.6 Hz, 1H, CH); 5.64 (d, J$_{HP}$=6.6 Hz, 1H, CH); 6.51 (br, 1H, NH); 6.77 (d, J$_{HP}$=6.6 Hz, 1H, CH); 6.92-7.67 (m, 15H); 9.10 (br, 1H, NH). $^{31}$P{$^1$H} NMR (CD$_2$Cl$_2$), d: 68.7 (s).

Example 1.5

[RuCl(p-cymene) ((S)-1-((R)-2-diphenylphosphino) ferrocenylethylamine))]Cl (5)

Yield=88%. $^{31}$P{$^1$H} NMR (CD$_2$Cl$_2$), d: 33.1 (s).

Example 2

General Procedure for Catalytic Hydrogenation of Ketones and Aldehydes

In a typical catalytic hydrogenation procedure, a weighed amount of the respective aminophosphine salt and KO$^t$Bu were added to a solution of the substrate in 2-propanol under hydrogen gas. The pressure was adjusted to the desired value and the reaction progress was monitored using TLC or NMR. After completion of the reaction, the solvent was removed by evaporation under reduced pressure. The alcohols were purified by filtering a hexane solution of the crude product through a pad of silica, then removing the hexane under reduced pressure. The conversion and purity of the alcohol products was assessed using NMR.

Discussion

The ruthenium aminophosphine salts [RuCl(p-cymene)(Ph$_2$PCH$_2$CH$_2$NH$_2$)]Cl (1), [RuCl(p-cymene)(i-Pr$_2$PCH$_2$CH$_2$NH$_2$)]Cl (2), [RuCl(p-cymene)(t-Bu$_2$PCH$_2$CH$_2$NH$_2$)]Cl (3), [RuCl(p-cymene){(R,R)(2-(diphenylphosphino)-1-phenylpropan-2-amine}]Cl (4) and [RuCl(p-cymene)((S)-1-((R)-2-diphenylphosphino)ferrocenylethylamine))]Cl (5) were prepared by refluxing a mixture of the respective aminophosphine ligand and [RuCl$_2$(p-cymene)]$_2$ in toluene was refluxed for 6 hours. Even though aminophosphine:ruthenium ratios of 2:1 and 4:1 were used in the preparations, only [RuCl(p-cymene)(aminophosphine)] Cl resulted, with only trace amounts of RuCl$_2$(aminophosphine)$_2$ being detected. The [RuCl(p-cymene)(aminophosphine)]Cl salts were soluble in polar organic solvents such as tetrahydrofuran, CH$_2$Cl$_2$, chloroform, ethanol and methanol. They were insoluble in toluene, benzene, ether and hexanes. Compounds 2 and 3 were also fairly soluble in water, whereas 1, 4 and 5 were sparingly soluble.

The effectiveness of these new catalysts for the hydrogenation of ketones and aldehydes was investigated. The results are summarized in Tables 1 to 3 as previously described.

In summary, this work in the present disclosure shows that ruthenium-aryl-aminophosphine complexes represent a very effective class of catalysts for hydrogenation of carbonyl substrates under very mild reaction conditions. It has also been demonstrated that ruthenium-aryl-aminophosphine complexes are air-stable and use only one stoichiometric equivalent of the aminophosphine ligand per ruthenium.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

HYDROGENATION OF CARBONYL COMPOUNDS USING [RUCl(p-CYMENE)(Ph$_2$PCH$_2$CH$_2$NH$_2$)]Cl/t-BUOK (1:10) AS CATALYST IN 2-PROPANOL (10 ATM. H$_2$) AT ROOM TEMPERATURE.[a]

| entry | substrate | S:C | time (h) | conv (%) |
|---|---|---|---|---|
| 1 | acetophenone | 2100 | 1.5 | 100 |
| 2 | benzophenone | 1000 | 2 | 100 |
| 3[b] | 4-tert-butylcyclohexanone | 700 | 2 | 100 |
| 4[c] | hex-5-en-2-one | 900 | 3 | 100 |
| 5[c] | benzalacetone | 1000 | 2 | 100 |
| 6[d] | norcamphor | 900 | 17 | 95 |
| 7 | benzaldehyde | 1000 | 4 | 100 |
| 8 | acetylferrocene | 5000 | 6 | 100 |

[a]A weighed amount of the catalyst and KO$^t$Bu were added to a solution of the substrate in 2-propanol and the mixture stirred at room temperature under hydrogen gas. Yields are based on the amount of substrate.
[b]Ratio of cis:trans alcohol = 4:1;
[c]only carbonyl group is reduced;
[d]ratio of endo:exo = 3:1.

TABLE 2

HYDROGENATION OF CARBONYL COMPOUNDS USING [RUCl(p-CYMENE)(i-Pr$_2$PCH$_2$CH$_2$NH$_2$)]Cl/t-BUOK (1:10) AS CATALYST IN 2-PROPANOL (10 ATM. H$_2$) AT ROOM TEMPERATURE.[a]

| entry | substrate | S:C | time (h) | conv (%) |
|---|---|---|---|---|
| 1 | acetophenone | 5000 | 4 | 100 |
| 2[b] | 4-tert-butylcyclohexanone | 700 | 5 | 100 |
| 3[c] | hex-5-en-2-one | 900 | 3 | 100 |
| 4[d] | norcamphor | 900 | 17 | 60 |
| 5 | benzaldehyde | 1000 | 4 | 100 |

[a]A weighed amount of the catalyst and KO$^t$Bu were added to a solution of the substrate in 2-propanol and the mixture stirred at room temperature under hydrogen gas. Yields are based on the amount of substrate.
[b]Ratio of cis:trans alcohol = 7:3;
[c]only carbonyl group is reduced;
[d]ratio of endo:exo = 7:3.

TABLE 3

HYDROGENATION OF ACETOPHENONE USING 3, 4 AND 5 AS CATALYST IN 2-PROPANOL (10 ATM. H$_2$) AT ROOM TEMPERATURE.[a]

| entry | substrate | catalyst | S:C | time (h) | conv (%) | e.e. |
|---|---|---|---|---|---|---|
| 1 | acetophenone | 3 | 1000 | 24 | 95 | — |
| 2 | acetophenone | 4 | 1000 | 8 | 100 | 5% (R) |

TABLE 3-continued

HYDROGENATION OF ACETOPHENONE USING 3, 4 AND 5 AS CATALYST IN 2-PROPANOL (10 ATM. H$_2$) AT ROOM TEMPERATURE.[a]

| entry | substrate | catalyst | S:C | time (h) | conv (%) | e.e. |
|---|---|---|---|---|---|---|
| 3 |  | 5 | 1000 | 0.5 | 100 | 25% (R) |

[a]A weighed amount of the catalyst and KO$^t$Bu were added to a solution of the substrate in 2-propanol and the mixture stirred at room temperature under hydrogen gas. Yields are based on the amount of substrate.

FULL CITATIONS FOR DOCUMENTS REFERRED TO IN THE SPECIFICATION (1) (a) Mikami, K.; Korenaga, T.; Terada, M.; Ohkuma, T.; Pham, T.; Noyori, R. *Angew. Chem.*, Int. Ed. 1999, 38, 495-497. (b) Doucet, H.; Ohkuma, T.; Murata, K.; Yokozawa, T.; Kozawa, M.; Katayama, E.; England, A. F.; Ikariya, T.; Noyori, R. *Angew. Chem.*, Int. Ed. 1998, 37, 1703-1707. (c) Ohkuma, T.; Ooka, H.; Ikariya, T.; Noyori, R. *J. Am. Chem. Soc.* 1995, 117, 10417-10418.

(2) (a) Ohkuma, T.; Koizumi, M.; Doucet, H.; Pham, T.; Kozawa, M.; Murata, K.; Katayama, E.; Yokozawa, T.; Ikariya, T.; Noyori, R. *J. Am. Chem. Soc.* 1998, 120, 13529-13530. (b) Ohkuma, T.; Doucet, H.; Pham, T.; Mikami, K.; Korenaga, T.; Terada, M.; Noyori, R. *J. Am. Chem. Soc.* 1998, 120, 1086-1087. (c) Ohkuma, T.; Ooka, H.; Yamakawa, M.; Ikariya, T.; Noyori, R. *J. Org. Chem.* 1996, 61, 4872-4873.

(3) (a) Abdur-Rashid, K.; Lough, A. J.; Morris, R. H. *Organometallics* 2001, 20, 1047-1049. (b) Abdur-Rashid, K.; Lough, A. J.; Morris, R. H. *Organometallics* 2000, 19, 2655-2657.

(4) (a) PCT Int. Appl. WO 02/22526 A2. (b) Abdur-Rashid, K.; Guo, R.; Lough, A. J.; Morris, R. H. *Adv. Synth. Catal.* 2005, 347, 571-579. (c) Guo, R.; Lough, A. J.; Morris, R. H.; Song, D. *Organometallics* 2004, 23, 5524-5529. (d) Guo, R.; Lough, A. J.; Morris, A. J.; Song, D. *Organometallics* 2005, 24 3354-3354.

(5) (a) Standfest-Hauser, C.; Slugove, C.; Mereiter, K.; Schmid, R.; Kirchner, K.; Xiao, L.; Weissensteiner, W. J. *J. Chem. Soc., Dalton Trans.* 2001, 2989-2995. (b) Liptau, P.; Carmona, D.; Oro, L. A.; Lahoz, F. J.; Kehr, G.; Erker, G. *Eur. J. Inorg. Chem.* 2004, 4586-4590.

We claim:

1. A process for the reduction of compounds comprising one or more carbon-oxygen (C=O) double bonds comprising contacting the compound with hydrogen gas and a catalyst comprising a ruthenium-aryl-aminophosphine complex in the presence of a base.

2. The process according to claim 1, wherein the compound comprising one or more carbon-oxygen (C=O) double bonds is a compound of formula (I):

(I)

wherein,

R$^1$ and R$^2$ each simultaneously or independently are selected from H, C$_{2-20}$alkenyl, C$_{2-20}$alkenyl, C$_{3-20}$cycloalkyl, C$_{3-20}$cycloalkenyl, C$_{6-14}$aryl and heteroaryl, said latter 7 groups being optionally substituted, or R$^1$ and R$^2$ are linked to form, together with the carbon atom to which they are attached, an optionally substituted monocycle or optionally substituted polycyclic ring system;

one or more of the carbon atoms in the alkyl, alkenyl, alkynyl, cycloalkyl and cycloalkenyl groups is optionally replaced with a heteromoiety selected from O, S, N, NR$^c$, PR$^c$, SiR$^c$ and SiR$^c$R$^d$;

the optional substituents are selected from =O, halo, OR$^c$, NR$^c$R$^d$ or R$^e$;

R$^c$ and R$^d$ are simultaneously or independently selected from H, fluoro-substituted-C$_{1-6}$ alkyl, C$_{1-6}$alkyl, C$_{2-6}$alkenyl, C$_{2-6}$alkynyl, C$_{6-14}$aryl and C$_{1-6}$alkylene C$_{6-14}$aryl; and R$^e$ is selected from H, fluoro-substituted-C$_{1-6}$alkyl, C$_{1-6}$alkyl, C$_{2-6}$alkenyl, C$_{2-6}$alkynyl, C$_{6-14}$ aryl and C$_{1-6}$alkyleneC$_{6-14}$aryl, and the process provides a compounds of formula (I'):

(I')

wherein R$^1$ and R$^2$ are defined as in formula (I).

3. The process according to claim 2, wherein R$^1$ and R$^2$ are different and the compound of formula (I') is chiral.

4. The process according to claim 1, wherein the ruthenium-aryl-aminophosphine complex is of the formula (II):

[RuX(A)(PNH$_2$)]X  (II)

wherein

A is optionally substituted C$_{6-14}$aryl or heteroaryl;

(PNH$_2$) represents an aminophosphine ligand of formula (III):

(III)

wherein

R$^3$ and R$^4$ each simultaneously or independently are selected from H, C$_{1-20}$alkyl, C$_{2-20}$alkenyl, C$_{2-20}$alkynyl, C$_{3-20}$cycloalkyl, C$_{3-20}$cycloalkenyl, C$_{6-14}$aryl, heteroaryl, OR$^5$ and NR$^5$R$^6$, said latter 9 groups being optionally substituted, or R$^3$ and R$^4$ are linked together to form an optionally substituted monocyclic or polycyclic, system having 4 or more atoms, including the phosphorous atom to which said groups are bonded, and in which one or more carbon atoms in said monocyclic or polycyclic ring system is optionally replaced with a heteromoiety selected from O, S, N, NR$^5$, SiR$^5$ and SiR$^5$R$^6$; L is selected from C$_{1-10}$alkylene, C$_{2-10}$alkenylene, C$_{2-10}$alkynylene, (C$_{6-14}$arylene)$_m$, C$_{1-10}$ alkylene-C$_{6-14}$arylene, C$_{6-14}$arylene-C$_{1-10}$alkylene and C$_{1-10}$alkylene-(C$_{6-14}$arylene)$_m$-C$_{1-10}$ alkylene, said latter 7 groups being optionally substituted;

m is 1, 2 or 3;

the optional substituents are selected from one or more of halo, OR$^5$, NR$^5$R$^6$ and R$^7$; and R$^5$ and R$^6$ are simultaneously or independently selected from H, fluoro-substituted-C$_{1-6}$ alkyl, C$_{1-6}$alkyl, C$_{2-6}$alkenyl, C$_{2-6}$alkynyl, C$_{6-14}$aryl and C$_{1-6}$alkylene C$_{6-14}$aryl; and R$^7$ is selected from fluoro-substituted-C$_{1-6}$alkyl, C$_{2-6}$alkenyl, C$_{2-6}$alkynyl, C$_{6-14}$ aryl and C$_{1-6}$alkyleneC$_{6-14}$aryl.

5. The process according to claim 4, wherein R$^3$ and R$^4$ each simultaneously or independently are selected from H, $C_{1-10}$alkyl, $C_{2-10}$alkenyl, $C_{2-10}$ alkynyl, $C_{3-10}$cycloalkyl, $C_{3-10}$cycloalkenyl, $C_{6-10}$aryl, heteroaryl, $OR^5$, $NHR^5$ and $NR^5R^6$, said latter 10 groups being optionally substituted, or $R^3$ and $R^4$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or bicyclic ring system is optionally replaced with a heteromoiety selected from O, S, N, NH and $NC_{1-4}$alkyl.

6. The process according to claim 5, wherein $R^3$ and $R^4$ each simultaneously or independently are selected from H, $C_{2-6}$alkenyl, $C_{2-6}$alkynyl, $C_{3-6}$cycloalkyl, $C_{3-6}$cycloalkenyl and $C_{6-10}$aryl said latter 6 groups being optionally substituted, or $R^3$ and $R^4$ are linked together to form an optionally substituted monocyclic or bicyclic, saturated, unsaturated and/or aromatic ring system having 4 to 10 atoms, including the phosphorous atom to which said groups are bonded.

7. The process according to claim 6, wherein $R^3$ and $R^4$ each simultaneously or independently are selected from H, $C_{1-6}$alkyl, $C_{2-6}$alkenyl, $C_{2-6}$alkynyl, $C_{3-6}$cycloalkyl and $C_{6-10}$aryl said latter 6 groups being optionally substituted, or $R^3$ and $R^4$ are linked together to form an optionally substituted monocyclic or bicyclic, saturated, unsaturated and/or aromatic ring system having 4 to 10 atoms, including the phosphorous atom to which said groups are bonded.

8. The process according to claim 7, $R^3$ and $R^4$ each simultaneously or independently are selected from phenyl and $C_{1-6}$alkyl.

9. The process according to claim 8, wherein $R^3$ and $R^4$ each simultaneously or independently are selected phenyl, methyl, ethyl, n-propyl, isopropyl, sec-butyl, tert-butyl and n-butyl.

10. The process according to claim 4, wherein L is selected from $C_{1-6}$ alkylene, $C_{2-6}$alkenylene and $(C_{6-14}$arylene$)_m$, said latter 3 groups being optionally substituted, and m is 1 or 2.

11. The process according to claim 10, wherein L is $C_{1-6}$alkylene being either unsubstituted or substituted with one or two halo or $R^7$, wherein $R^7$ is selected from fluoro-substituted-$C_{1-6}$alkyl, $C_{1-6}$alkyl, $C_{6-14}$aryl and $C_{1-4}$-alkylene$C_{6-14}$aryl.

12. The process according to claim 11, wherein L is $C_{1-4}$-alkylene, being either unsubstituted or substituted with one or two halo or $R^7$, wherein $R^7$ is selected from fluoro-substituted-$C_{1-6}$alkyl, $C_{1-6}$alkyl, $C_{6-14}$aryl and $C_{1-4}$alkylenephenyl.

13. The process according to claim 12, wherein $R^7$ is selected from phenyl, methyl, benzyl or $CF_3$.

14. The process according to claim 10, wherein L is unsubstituted $C_{2-3}$alkylene.

15. The process according to claim 10, wherein L is optionally substituted biphenylenyl or binaphthylenyl.

16. The process according to claim 10, wherein L is optionally substituted $C_{6-14}$arylene or $C_{6-14}$arylene-$C_{1-6}$alkylene.

17. The process according to claim 16, wherein the $C_{6-14}$arylene is selected from phenylenyl, naphthylenyl and metallocenyl, the $C_{1-6}$ alkylene is selected from methylene and ethylene; and the optional substituent is selected from $CH_3$ and $CF_3$.

18. The process according to claim 17, wherein the metallocenyl is ferrocenyl.

19. The process according to claim 16, wherein bonds linking the phenylenyl, naphthylenyl and metallocenyl are located at positions ortho to each other.

20. The process according to claim 4, wherein the optional substituents on the aminophosphine of formula III are selected from one or more of halo, OH, $NH_2$, $NHR^5$, $OR^5$, $N(R^5)(R^6)$ and $R^7$, in which $R^5$, $R^6$ and $R^7$ are simultaneously or independently selected from fluoro-substituted-$C_{1-4}$alkyl, $C_{1-4}$-alkyl, $C_{2-4}$alkenyl, phenyl and $C_{1-4}$alkylenephenyl, specifically methyl, benzyl and phenyl.

21. The process according to claim 20, wherein $R^5$, $R^6$ and $R^7$ are simultaneously or independently selected from methyl, benzyl and phenyl.

22. The process according to claim 4, wherein A is a monocyclic or bicyclic aromatic group having between 6-10 carbon atoms and is optionally substituted with 1 to 3 substituents independently selected from fluoro-substituted-$C_{1-6}$alkyl, $C_{1-6}$alkyl, $C_{2-6}$alkenyl and $C_{6-10}$aryl.

23. The process according to claim 22, wherein A is a phenyl group optionally substituted with 1 to 3 substituents independently selected from fluoro-substituted-$C_{1-6}$alkyl, $C_{2-6}$alkenyl and $C_{6-10}$aryl.

24. The process according to claim 23, wherein A is a phenyl group optionally substituted with 1 to 3 substituents independently selected from fluoro-substituted-$C_{1-4}$alkyl, $C_{1-4}$alkyl and $C_{2-6}$alkenyl.

25. The process according to claim 23, wherein A is p-cymene.

26. The process according to claim 4, wherein X are the same or different and are selected from halo $HO^-$, $R^8O^-$ and $R^8C(O)O^-$, wherein $R^8$ is H or $C_{1-6}$alkyl.

27. The process according to claim 26, wherein X is chloro.

28. The process according to claim 4, wherein the ruthenium aryl-aminophosphine complex of formula II is selected from 29. The process according to claim 1, wherein the base is an organic non-coordinating base, an alkaline or alkaline-earth metal carbonate, a carboxylate salt or an alcoholate or hydroxide salt.

30. The process according to claim 29, wherein the base is an alcoholate or a hydroxide salt selected from compounds of formula $(R^9O)_2M'$ and $R^9OM'$, in which M' is an alkaline or alkaline-earth metal and $R^9$ is hydrogen or $C_{1-6}$alkyl.

31. The process according to claim 30, wherein $R^9$ is t-butyl and M' is potassium.

32. The process according to claim 1, wherein the process is performed in a polar organic solvent.

33. The process according to claim 32, wherein the solvent is selected from tetrahydrofuran, diethyl ether, primary and secondary alcohols, chlorinated solvents and mixtures thereof.

34. The process according to claim 1, wherein the hydrogen gas is used at a pressure in the range of about 1 atm to about 100 atm.

35. The process according to claim 34, wherein the hydrogen gas is used at a pressure in the range of about 7 atm to about 13 atm.

36. The process according to claim 35, wherein the hydrogen gas is used at a pressure of 10 atm.

37. The process according to claim 2, wherein, in the compounds of formula (I) and (I'), $R^1$ and $R^2$ each simultaneously or independently are selected from H, $C_{1-10}$alkyl, $C_{2-10}$alkenyl, $C_{2-10}$alkenyl, $C_{3-10}$cycloalkyl, $C_{3-10}$cycloalkenyl and $C_{6-10}$aryl, said latter 7 groups being optionally substituted, or $R^1$ and $R^2$ are linked to form, together with the carbon atom to which they are attached, an optionally substituted monocycle or optionally substituted polycyclic ring system;

the optional substituents are selected from =O, halo, $OR^c$, $NR^cR^d$ or $R^e$;

$R^c$ and $R^d$ are simultaneously or independently selected from H, fluoro-substituted-$C_{1-4}$alkyl, $C_{1-4}$alkyl, $C_{2-4}$alkenyl, $C_{2-4}$alkynyl, $C_{6-10}$aryl and $C_{1-4}$alkylene $C_{6-10}$aryl; and $R^e$ is selected from fluoro-substituted-$C_{1-4}$alkyl, $C_{1-4}$alkyl, $C_{2-4}$alkenyl, $C_{2-4}$alkynyl, $C_{6-10}$aryl and $C_{1-4}$-alkylene$C_{6-10}$aryl.

38. The process according to claim 2, wherein, in the compounds of formula (I) and (I'), $R^1$ and $R^2$ each simultaneously or independently are selected from H, $C_{1-6}$alkyl, $C_{2-6}$alkenyl, $C_{2-6}$alkenyl, $C_{3-8}$cycloalkyl, $C_{3-8}$cycloalkenyl, ferrocenyl and phenyl, said latter 6 groups being optionally substituted, or $R^1$ and $R^2$ are linked to form, together with the carbon atom to which they are attached, an optionally substituted monocycle or optionally substituted polycyclic ring system;

the optional substituents are selected from =O, halo, $OR^c$, $NR^cR^d$ or $R^e$;

$R^c$ and $R^d$ are simultaneously or independently selected from H, $CF_3$, $CH_3$, phenyl and benzyl; and $R^e$ is selected from $CF_3$, $CH_3$, phenyl and benzyl.

* * * * *

UNITED STATES PATENT AND TRADEMARK OFFICE
CERTIFICATE OF CORRECTION

| | |
|---|---|
| PATENT NO. | : 7,772,445 B2 |
| APPLICATION NO. | : 12/168396 |
| DATED | : August 10, 2010 |
| INVENTOR(S) | : Chen et al. |

It is certified that error appears in the above-identified patent and that said Letters Patent is hereby corrected as shown below:

Column 15, line 58, replace "formula (1)" with --formula (I)--;

Column 15, line 65, insert --$C_{1-20}$ alkyl,-- before --$C_{2-20}$alkenyl--;

Column 16, line 13, replace "fluoro-substituted-$C_{1-6}$ alkyl"(remove space) with --fluoro-substituted-$C_{1-6}$alkyl--;

Column 16, line 19, replace "formula (1')" with --formula (I)--;

Column 16, line 27, replace "formula (1)" with --formula (I)--;

Column 16, line 29, replace "formula (1')" with --formula (I)--;

Column 16, line 31, replace "formula (11)" with --formula (II)--;

Column 16, line 37, replace "formula (111)" with --formula (III)--;

Column 16, line 61, replace "fluoro-substituted-$C_{1-6}$ alkyl" (remove space) with --fluoro-substituted-$C_{1-6}$alkyl--;

Column 17, line 13, insert "$C_{1-6}$alkyl," before --$C_{2-6}$alkenyl--; and

Column 18, line 25, replace "formula (11)" with --formula (II)--;

Column 19, line 28, replace "$C_{2-10}$alkenyl" with --$C_{2-10}$alkynyl--;

Column 20, line 17, replace "$C_{2-10}$alkenyl" with --$C_{2-10}$alkynyl--;

Signed and Sealed this

Thirtieth Day of November, 2010

David J. Kappos
*Director of the United States Patent and Trademark Office*